United States Patent [19]

Schrenker

[11] 4,404,845

[45] Sep. 20, 1983

[54] THERMAL REGULATOR FOR LIQUID CHROMATOGRAPHS

[75] Inventor: Helge Schrenker, Karlsruhe, Fed. Rep. of Germany

[73] Assignee: Hewlett-Packard GmbH, Boeblingen, Fed. Rep. of Germany

[21] Appl. No.: 276,394

[22] Filed: Jun. 22, 1981

[30] Foreign Application Priority Data

Jul. 11, 1980 [DE] Fed. Rep. of Germany ....... 3026267

[51] Int. Cl.³ .................... G01N 31/00; B01D 15/08; F25B 29/00
[52] U.S. Cl. .............................. 73/61.1 C; 73/863.12; 165/26; 165/61; 210/198.2; 422/70
[58] Field of Search ................. 165/61, 64; 210/198.2, 210/656, 739, 742, 748; 55/197, 386; 73/23.1, 61.1 C, 61.1 R, 863.12; 422/70

[56] References Cited

U.S. PATENT DOCUMENTS

3,165,147  1/1965  Roof et al. ............................ 55/386
3,522,725  8/1970  Waters ............................. 73/61.1 C

*Primary Examiner*—William R. Cline
*Assistant Examiner*—John K. Ford
*Attorney, Agent, or Firm*—Stephen P. Fox

[57] ABSTRACT

A thermostat arrangement for the mobile phase and the separation column in a liquid chromatograph comprises a heat exchanger through which the mobile phase passes. The heat exchanger has a heating and/or cooling element and is arranged between a sample injection device and the entrance of the separation column. The heat exchanger serves to selectively heat or cool the ambient air surrounding the separation column.

2 Claims, 4 Drawing Figures

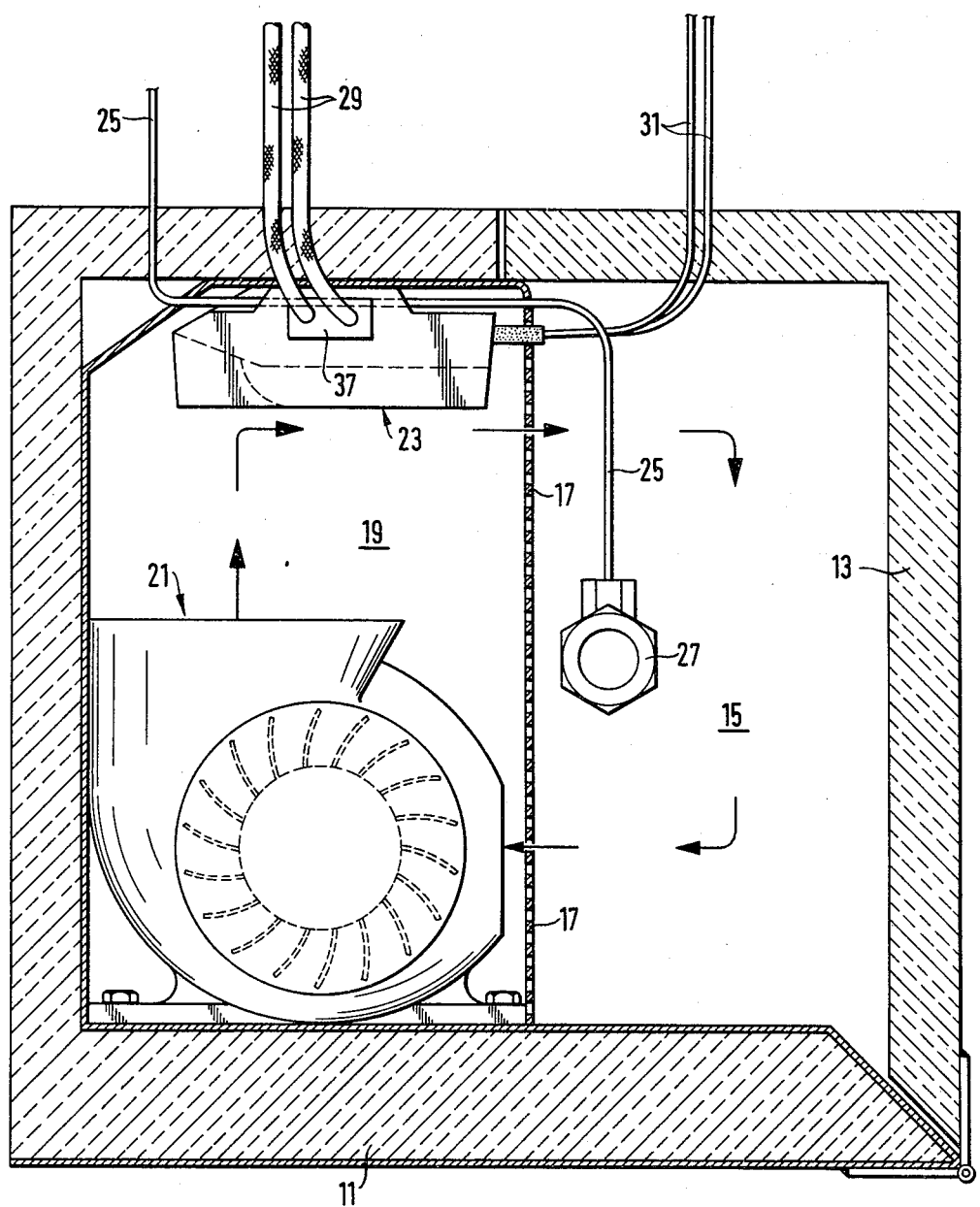

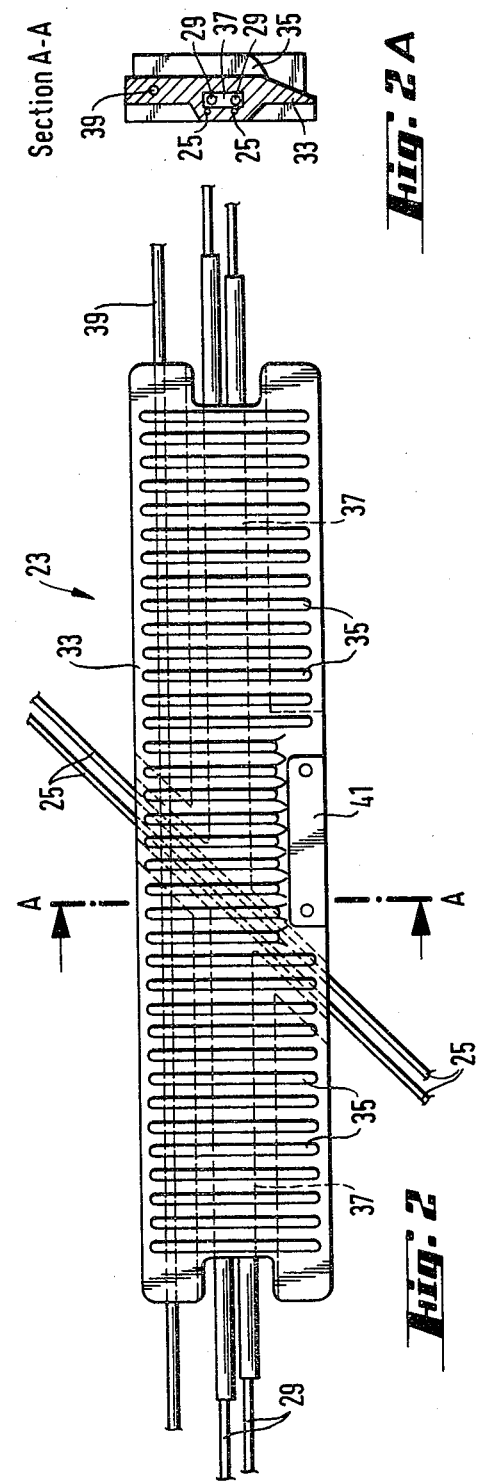

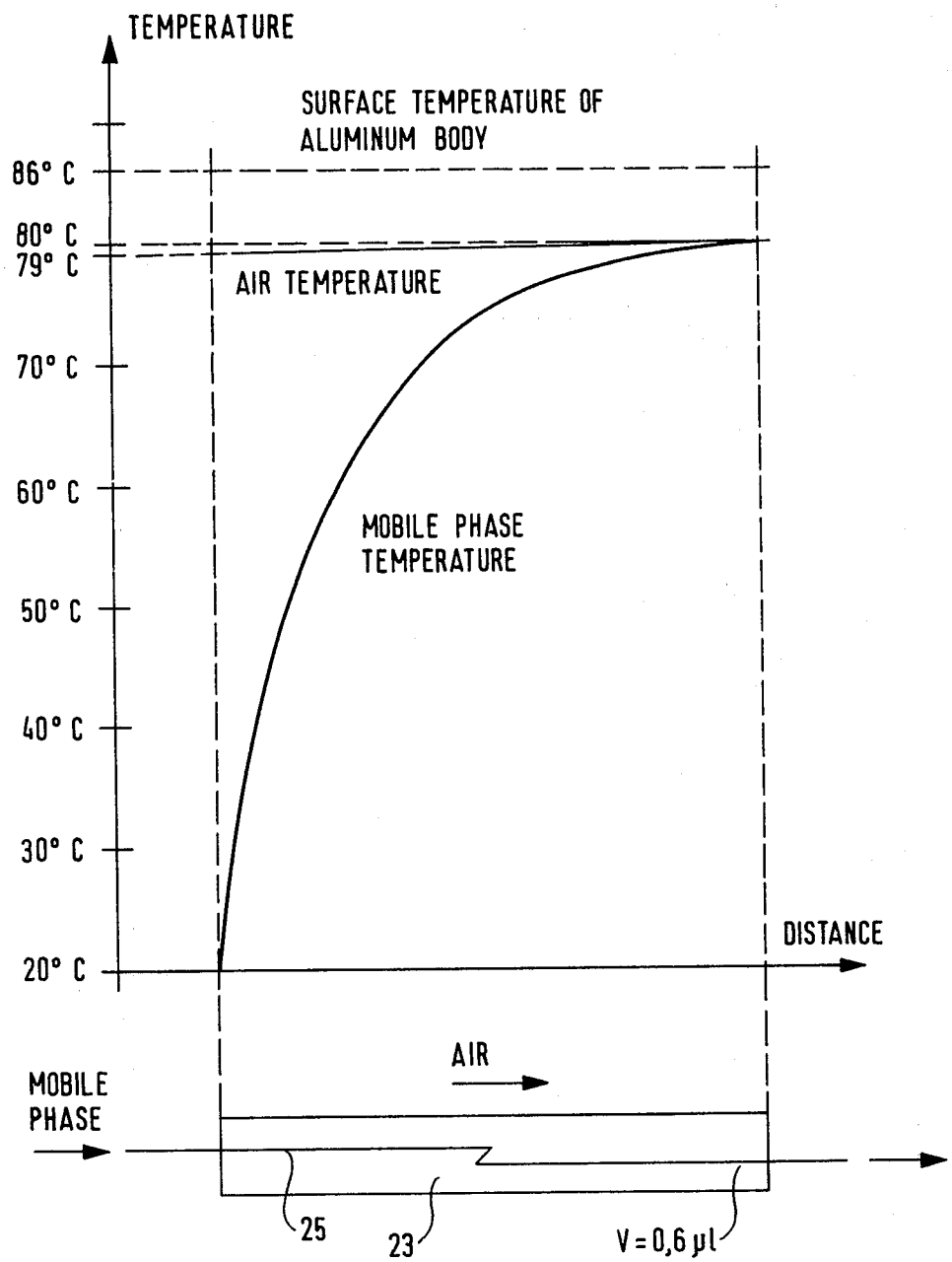

THERMAL REGULATOR FOR LIQUID CHROMATOGRAPHS

BACKGROUND OF THE INVENTION

The course of the operation process in the column of a liquid chromatograph is temperature dependent, e.g., the retention time may vary by 3 to 4% per degree Celsius temperature variation. The retention time is defined as the dwell duration of the substance in the separation column, which dwell duration is necessary for identifying the substance. Thus, on the one hand it is possible to use the column temperature as a parameter for optimizing the separation process. On the other hand, however, it is necessary that this temperature is kept constant at a defined value over the whole longitudinal extent of the column.

There are substantially three well known methods for keeping the temperature in the separation column constant. The most common method is to house the column within an air convection thermal regulator, the inner air temperature of which is controlled (see e.g. Hewlett-Packard Technical Information Bulletin entitled "High-Speed Liquid Chromatograph Model 1010A", April, 1973). Another method is to mount the separation column within an aluminum body, the temperature of which is controlled (see e.g. Varian Product Bulletin SEP-2182A entitled "5000 Series Liquid Chromatographs", USA 20M 978). According to the third method the separation column is concentrically mounted within a tube through which a liquid such as water flows, which liquid is kept at constant temperature by means of a liquid convection thermal regulator (i.e., Snyder and J. J. Kirkland, *Introduction to Modern Liquid Chromatography*, page 128, John Wiley & Sons, 1974).

In any of the aforementioned arrangements substantial axial and radial temperature gradients can occur in the separation column, since the mobile phase enters the column at ambient temperature and is heated to column temperature there. The required amount of heat must be supplied through the colum wall which usually consists of stainless steel. The transmission of heat from the column wall to the mobile phase, and the thermal conductivity of the mobile phase flowing laminarly through the stationary phase are not sufficient to assimilate the raised temperature present at the column entrance. This causes the above mentioned temperature gradient in the separation column. For example, in an air thermal regulator at a temperature of 80° C., temperature differences up to 20° C. were measured between column entrance and column exit at a column of 25 cm length and 4.6 mm inner diameter when 4 ml/min of water was flowing through it. Since the temperature gradients are dependent on the type of the column and the position thereof within the thermal regulator, consistency of the analysis result is difficult to achieve. Moreover, the separation capability of the column is substantially affected by the temperature gradients.

In order to avoid these drawbacks it has already been proposed to heat the mobile phase before it enters the separation column (CZ-Chemie-Technik 1 (1972) pp. 73–78). According to this proposal, the heat required for the heat exchanger is taken from the ambient air of the thermal regulator. Due to a poor heat transmission this requires a relatively large heat exchanger volume of about 0.6 ml. The development of liquid chromatography, however, has led to short and small volume separation columns which often are operated with solvent gradients, i.e., the composition of the mobile phase varies during separations. Additionally, it is desired to heat not only the solvent but also the sample substance, i.e., the heat exchanger should be located between the sample injection device and the column entrance. In both aforementioned cases, however, a relatively large heat exchanger volume is not tolerable. It must not be biffer than a few microliters.

SUMMARY OF THE INVENTION

It is an object of the invention to provide a thermal regulator for the mobile phase and the separation column in a liquid chromatograph which avoids the occurrence of disadvantageous temperature gradients and requires only a small heat exchanger volume.

According to the preferred embodiment of the invention, the heat exchanger through which the mobile phase passes has a heating and/or cooling element and is arranged between the sample injection device and the entrance of the separation column. The heat exchanger serves to selectively heat or cool the ambient air surrounding the separation column.

Preferably the heat exchanger comprises a capillary tube through which the mobile phase passes. The tube is together with the heating and/or cooling element sealed within a molded radiator body of heat conducting material. The capillary tube has an inner diameter of less than 0.5 mm and a volume of less than 2 $\mu l$ within the heat exchanger. A laminar liquid flow is to be expected in the usual capillary tubes of about 0.3 mm inner diameter with the low flow speeds usual in liquid chromatography (below 5 ml/min). However, it has unexpectedly turned out that at such low flow speeds in capillary tubes of less than 0.15 mm inner diameter a flow mode is generated which is similar to a turbulent flow, in that there are radial flow components within the tube. This causes a substantially enhanced heat transmission from the tube wall to the mobile phase.

The capillary tube is situated within the radiator body in close proximity to the heating and/or cooling element in such a manner that a variation of the flow rate of the mobile phase within a range of 0 to 5 ml/min causes a temperature deviation of less than ±2° C.

In order to measure the actual temperature of the heat exchanger a temperature sensor may be mounted on the surface of the radiator body close to the capillary tube and to the heating and/or cooling element.

BRIEF DESCRIPTION OF THE DRAWINGS

FIG. 1 shows a cross section of a thermal regulator according to one embodiment of the invention.

FIGS. 2 and 2A are, respectively, a plan view and a cross section view of the heat exchanger body used in the thermal regulator according to FIG. 1.

FIG. 3 is a graphical representation of the temperature variations along the heat exchanger according to FIG. 2.

DESCRIPTION OF THE PREFERRED EMBODIMENT

Referring to FIG. 1, a housing 11 of heat insulating material comprises a cover 13 which can be opened in order to allow access to a column compartment 15. A wall 17 penetrable by air (e.g., made of punched sheet metal) separates column compartment 15 from a heating and fan compartment 19.

A radial fan 21 is located in compartment 19. Fan 21 has in the present embodiment a drum length of 300 mm and a flow rate of about 20 ls$^{-1}$. The air flow caused by fan 21 is indicated by arrows.

Positioned in the air flow path within housing 11 is a heat exchanger body 23 which is preferrably an aluminum body having ribs on its bottom surface. The heat exchanger body 23 can be connected to wall 17 in a heat conducting manner. A capillary tube 25 leads through heat exchanger body 23. The mobile phase and the sample substance flow through capillary tube 25 to a separation column 27 located in column compartment 15. Electric cables 29 and 31 lead to heat exchanger body 23 for supplying a heater and a temperature sensor. Further details of separation column 27, the tubes connected thereto, and the rest of the solvent circuit are not shown since they are arranged in the commonly known manner.

FIGS. 2 and 2A show heat exchanger body 23 in plan view (as seen from the bottom in FIG. 1) as well as a cross section in detail. A resistor heating element 37 with supply lines 29, a cooling tube 39 and two capillary tubes 25 for the mobile phase and the samples are sealed within a molded aluminum body 33 having cooling ribs 35. Capillary tubes 25 consist of V4A-steel of 0.13±0.02 mm inner diameter and 1.5 mm outer diameter and are sealed within aluminum body 33 for a distance of about 90 mm. They cross resistance heating element 37 in close proximity thereto at an angle of about 45°.

Resistance heating element 37 is a flat tube heater providing 110 watts of internal power. It is sealed within aluminum body 33 along an effective length of about 250 mm (corresponding to a surface of about 8000 mm$^2$). Cooling tube 39 is a V4A-steel tube of 2 mm inner diameter and 3 mm outer diameter and of a length of about 290 mm. The required flow rate of the cooling medium within tube 39 is 0.1–0.3 liters/min.

Reference numeral 41 indicates a schematically shown temperature sensor. The position thereof relative to capillary tubes 25, cooling tube 39 and resistance heating element 37 is chosen in such a manner that the surface temperature is varied as little as possible when the flow speed of the mobile phase varies and also when the supplied heating power varies due to temperature control.

The provision of resistance heating element 37 and of cooling tube 39 within heat exchanger body 23 allows temperature control of the mobile phases on values above as well as below room temperature.

FIG. 3 shows a typical example of the temperature of the air passing heat exchanger body 23 and of the mobile phase passing through it, as a function of the active length of heat exchanger body 23. It is an essential fact that at the end of the active length of the heat exchanger the temperatures of the air and the mobile phase are equal. The surface temperature of aluminum body 33 is a few degrees higher. However, this is not disadvantageous since this temperature difference may be taken into account by correction in an associated control circuit.

I claim:

1. A thermal regulator for the mobile phase and the separation column in a liquid chromatograph having a sample injection device, said thermal regulator comprising:

a heat exchanger including a capillary tube through which the mobile phase passes, said heat exchanger being disposed between the sample injection device and the entrance of the separation column and containing a heating element and a cooling element for respectively heating and cooling ambient air surrounding the separation column;

said capillary tube, said heating element and said cooling element being sealed within a molded radiator body of heat conducting material disposed in contact with ambient air surrounding said separation column;

said capillary tube having an inner diameter of less than 0.15 mm and a volume of less than 2 µl within the heat exchanger;

whereby a variation of the flow rate of the mobile phase within a range of 0 to 5 ml/min causes a temperature deviation of less than ±2 degrees C.

2. A thermal regulator according to claim 1, wherein a temperature sensor is mounted on the surface of the radiator body close to the capillary tube and to the heating element and the cooling element.

* * * * *

UNITED STATES PATENT AND TRADEMARK OFFICE
CERTIFICATE OF CORRECTION

PATENT NO. : 4,404,845
DATED : September 20, 1983
INVENTOR(S) : Helge Schrenker

It is certified that error appears in the above—identified patent and that said Letters Patent is hereby corrected as shown below:

Column 2 on the Title Page, under Abstract, line 1, delete "thermostat arrangement" and substitute -- thermal regulator --;

Column 1, line 52, delete "at" and substitute -- in --;

Column 2, line 8, delete "biffer" and substitute -- bigger --.

Signed and Sealed this

Twenty-second Day of November 1983

[SEAL]

Attest:

GERALD J. MOSSINGHOFF

Attesting Officer

Commissioner of Patents and Trademarks